US010900972B2

(12) United States Patent
Stapels et al.

(10) Patent No.: US 10,900,972 B2
(45) Date of Patent: Jan. 26, 2021

(54) METHODS FOR ABSOLUTE QUANTIFICATION OF LOW-ABUNDANCE POLYPEPTIDES USING MASS SPECTROMETRY

(71) Applicant: Genzyme Corporation, Cambridge, MA (US)

(72) Inventors: Martha Stapels, Milford, MA (US); Michelle Busch, Harvard, MA (US)

(73) Assignee: GENZYME CORPORATION, Cambridge, MA (US)

( * ) Notice: Subject to any disclaimer, the term of this patent is extended or adjusted under 35 U.S.C. 154(b) by 218 days.

(21) Appl. No.: 15/996,031

(22) Filed: Jun. 1, 2018

(65) Prior Publication Data

US 2019/0004059 A1 Jan. 3, 2019

Related U.S. Application Data

(60) Provisional application No. 62/514,587, filed on Jun. 2, 2017.

(51) Int. Cl.
*G01N 33/68* (2006.01)

(52) U.S. Cl.
CPC ..... *G01N 33/6848* (2013.01); *G01N 2458/15* (2013.01); *G01N 2560/00* (2013.01)

(58) Field of Classification Search
None
See application file for complete search history.

(56) References Cited

U.S. PATENT DOCUMENTS 8,271,207 B2  9/2012  Geromanos et al.
8,688,389 B2  4/2014  Geromanos et al.

FOREIGN PATENT DOCUMENTS

| CA | 2 487 821 A1 | 12/2002 |
| WO | WO-2003/089937 A2 | 10/2003 |
| WO | WO-2006/132994 A2 | 12/2006 |
| WO | WO-2006/133109 A1 | 12/2006 |
| WO | WO-2014/016586 A1 | 1/2014 |

OTHER PUBLICATIONS

Kong, A.T. et al. (May 2017; e.pub. Apr. 10, 2017). "MSFragger: Ultrafast and Comprehensive Peptide Identification in Mass Spectrometry-Based Proteomics," *Nature Methods* 14(5):513-520, twenty nine pages.
Silva, J.C. et al. (Jan. 2006; 2-pub. Oct. 11, 2005). "Absolute Quantification of Proteins by LCMS$^E$: A Virtue of Parallel MS Acquisition," *Mol. Cell Proteomics* 5(1):144-156.
International Search Report and Written Opinion of the International Searching Authority dated Aug. 13, 2018 for PCT Application No. PCT/US2018/035716 filed on Jun. 1, 2018, fifteen pages.
International Preliminary Report on Patentability dated Dec. 3, 2019, for PCT Application No. PCT/US2018/035716 filed on Jun. 1, 2018, 8 pages.

*Primary Examiner* — Xiaoyun R Xu
(74) *Attorney, Agent, or Firm* — Morrison & Foerster LLP

(57) ABSTRACT

The present invention provides methods for improved label-free absolute quantification of relatively low abundant polypeptides by liquid chromatography/mass spectrometry analysis of peptide products obtained from simple or complex polypeptide mixtures. The methods for absolute quantification include MS signals from a set of qualified ions of peptide products of a relatively high abundant polypeptide to improve quantification of a relatively low abundant polypeptide.

18 Claims, 6 Drawing Sheets

METHODS FOR ABSOLUTE QUANTIFICATION OF LOW-ABUNDANCE POLYPEPTIDES USING MASS SPECTROMETRY

CROSS-REFERENCE TO RELATED APPLICATIONS

This application claims priority to U.S. Provisional Application No. 62/514,587, filed Jun. 2, 2017, the disclosure of which is incorporated herein by reference in its entirety.

TECHNICAL FIELD

The present invention provides methods for absolute quantification of low-abundance polypeptides by liquid chromatography/mass spectrometry (LC/MS) analysis of peptide products obtained from simple or complex polypeptide mixtures.

BACKGROUND OF THE INVENTION

A diverse array of mass spectrometry (MS)-based techniques for polypeptide quantification are known in the art. For example, polypeptides may be quantified using metabolic-based techniques (e.g., stable isotope labeling using amino acids in cell culture (SILAC)), peptide standard-based techniques (e.g., selected reaction monitoring (SRM) and multiple reaction monitoring (MRM)), and label-based techniques (e.g., Tandem Mass Tags (TMT)). These methods have well documented drawbacks, such as limited sample sources for SILAC, extensive development and cost of SRM and MRM, and the additional sample processing and yield of relative abundances of label-based techniques.

MS-based label-free quantification techniques were developed to simplify MS-based polypeptide quantification methods and to circumvent some of the above-mentioned limitations. However, current label-free quantification techniques may suffer from low accuracy and high variability, and most label-free techniques may only provide a relative quantification ratio between two or more samples (e.g., spectral counting).

One approach for MS-based label-free absolute quantification of proteins involves using a protein standard to create a single point calibration measurement that is applied to subsequent mass spectrometry analyses for the absolute quantification of other proteins. J. C. Silva et al., *Mol Cell Proteomics*, 5, 144-56, 2006; U.S. Pat. No. 8,271,207. However, use of a single point calibration and differences created by separate enzymatic digestions of the sample and the protein standard may be major sources of quantification variability for this method.

Thus, there is a need in the art for improved MS-based label-free absolute quantification techniques that are sensitive, accurate, and precise, and can be applied to a diverse array of polypeptide samples in a high-throughput manner.

All references cited herein, including patent applications and publications, are incorporated by reference in their entirety.

BRIEF SUMMARY OF THE INVENTION

The present invention provides methods for label-free absolute quantification of low-abundance polypeptides in a sample comprising another polypeptide of relative high abundance. For example, the invention provides methods for quantifying low-abundance host cell proteins in a culture system, or downstream product thereof, comprising a host cell capable of producing a recombinant polypeptide, such as a therapeutic polypeptide. The methods use the concentration and peptide product MS signals of a high abundance polypeptide and peptide product MS signals of a low-abundance polypeptide to calculate the absolute quantity of the low-abundance polypeptide.

In one aspect, the present invention provides methods for absolute quantification of a first polypeptide in a sample comprising a plurality of polypeptides comprising the first polypeptide and a second polypeptide, wherein the first polypeptide is at least 10-fold lower in abundance than the second polypeptide, the method comprising: (a) analyzing peptide products of the plurality of polypeptides at a plurality of sample loading quantities using a liquid chromatography/mass spectrometry (LC/MS) technique to obtain MS signals of ions of the peptide products of the plurality of polypeptides at each of the plurality of sample loading quantities, wherein the plurality of sample loading quantities comprises a first sample loading quantity and a second sample loading quantity, and wherein the first sample loading quantity is greater than the second sample loading quantity; (b) calculating the average or sum of an MS signal for: (i) a top set of n number of qualified ions of peptide products of the first polypeptide with the highest MS signals at the first sample loading quantity (A); (ii) a top set of n number of qualified ions of peptide products of the second polypeptide with the highest MS signals at the second sample loading quantity (B); (iii) a middle set of m number of qualified ions of peptide products of the second polypeptide at the first sample loading quantity (C); and (iv) the middle set of qualified ions of peptide products of the second polypeptide at the second sample loading quantity (D), wherein A, B, C, and D are all calculated using the average or all calculated using the sum of the MS signal; and (c) determining an absolute quantity of the first polypeptide in the first sample loading quantity based on the following formula:

$$[(A)/(C)]*(\text{mole of the second polypeptide at the first loading quantity})*[(D)/(B)],$$

or mathematical equivalents thereof.

In another aspect, the present invention provides methods for absolute quantification of a first polypeptide in a sample comprising a plurality of polypeptides comprising the first polypeptide and a second polypeptide, wherein the first polypeptide is at least 10-fold lower in abundance than the second polypeptide, the method comprising: (a) obtaining MS signals of ions of peptide products of the plurality of polypeptides, wherein said MS signals of ions of the peptide products are obtained by analyzing the peptide products of the plurality of polypeptides using a liquid chromatography/ mass spectrometry (LC/MS) technique, wherein MS signals of the peptide products are obtained for each of a plurality of sample loading quantities comprising a first sample loading quantity and a second sample loading quantity, and wherein the first sample loading quantity is greater than the second sample loading quantity; (b) calculating the average or sum of an MS signal for: (i) a top set of n number of qualified ions of peptide products of the first polypeptide with the highest MS signals at the first sample loading quantity (A); (ii) a top set of n number of qualified ions of peptide products of the second polypeptide with the highest MS signals at the second sample loading quantity (B); (iii) a middle set of m number of qualified ions of peptide products of the second polypeptide at the first sample loading quantity (C); and (iv) the middle set of qualified ions of peptide products of the second polypeptide at the second sample loading quantity (D), wherein A, B, C, and D are all calculated using the average or all calculated using the sum of the MS signal; and (c) determining an absolute quantity of the first polypeptide in the first sample loading quantity based on the following formula:

$$[(A)/(C)]*(\text{mole of the second polypeptide at the first loading quantity})*[(D)/(B)],$$

or mathematical equivalents thereof.

In some embodiments, the average of the MS signal is used for determining the absolute quantity of the first polypeptide.

In some embodiments, the sum of the MS signal is used for determining the absolute quantity of the first polypeptide.

In some embodiments, the middle set of qualified ions of peptide products of the second polypeptide is selected based on quantification error of the qualified ions of peptide products of the second polypeptide from the plurality of sample loading quantities, or the first sample loading quantity and/or the second sample loading quantity.

In another aspect, the present invention provides methods for selecting a set of qualified ions of peptide products for absolute quantification of a first polypeptide in a sample comprising a plurality of polypeptides comprising the first polypeptide and a second polypeptide, wherein the first polypeptide is at least 10-fold lower in abundance than the second polypeptide, the method comprising: (a) analyzing the peptide products of the plurality of polypeptides at a plurality of sample loading quantities using a liquid chromatography/mass spectrometry (LC/MS) technique to obtain MS signals of ions of the peptide products of the plurality of polypeptides at each of the plurality of sample loading quantities, wherein the plurality of sample loading quantities comprises a first sample loading quantity and a second sample loading quantity, and wherein the first sample loading quantity is greater than the second sample loading quantity; and (b) selecting a middle set of m number of qualified ions of peptide products of the second polypeptide, wherein the middle set of qualified ions of peptide products of the second polypeptide is selected based on quantification error of the qualified ions of peptide products of the second polypeptide from the plurality of sample loading quantities, or the first sample loading quantity and/or the second sample loading quantity. In some embodiments, the methods further comprise selecting a top set of n number of qualified ions of peptide products of the second polypeptide with the highest MS signals at the second sample loading quantity.

In some embodiments, each of the top set of qualified ions of peptide products is different than each of the middle set of qualified ions.

In some embodiments, the MS signal is ionization intensity or peak height or peak area or peak volume.

In some embodiments, the methods further comprise obtaining the sample.

In some embodiments, the sample has been purified or enriched. In some embodiments, the methods further comprise processing the plurality of polypeptides in the sample to produce the peptide products. In some embodiments, processing the sample comprises one or more of the following: (a) centrifuging the sample to isolate the plurality of polypeptides; (b) purifying the plurality of polypeptides in the sample; (c) removing from the sample components incompatible with subsequent processing and the mass spectrometry analysis; (d) digesting the plurality of polypeptides to produce the peptide products; and (e) purifying the peptide products.

In some embodiments, the LC/MS technique comprises separating the peptide products via a liquid chromatography technique.

In some embodiments, the LC/MS technique comprises processing the obtained MS signals of the peptide products.

In some embodiments, the LC/MS technique further comprises one or more the following: (a) identifying the peptide products by amino acid sequence; (b) identifying the first polypeptide by a protein identifier; and (c) identifying one or more of the plurality of polypeptides by a protein identifier.

In some embodiments, the methods further comprise determining the absolute quantity of the second polypeptide.

In some embodiments, the first polypeptide is a host cell protein or a biomarker. In some embodiments, the first polypeptide is at least 100-fold lower in abundance than the second polypeptide.

In some embodiments, the second polypeptide is a recombinant polypeptide produced by a host cell or a therapeutic polypeptide or serum albumin. In some embodiments, the second polypeptide is expressed from a vector transfected into a host cell, such as a mammalian host cell, such as a Chinese Hamster Ovary (CHO) cell.

In some embodiments, the sample is a cell culture sample or a blood or a serum sample or a pharmaceutical product or an intermediate thereof.

In some embodiments, the peptide products of the plurality of polypeptides in the sample are obtained via sample digestion prior to analyzing the peptide products using the LC/MS technique. In some embodiments, the peptide products are tryptic peptide products of the plurality of polypeptides.

In some embodiments, the plurality of sample loading quantities comprises sample loading quantities in the range of about 0.1-25 µg total protein. In some embodiments, the first sample loading quantity is about 10 µg total protein. In some embodiments, the second sample loading quantity is about 0.5 µg to 10 µg, or 3 µg to 6 µg, or 1 µg, 2 µg, 3 µg, 4 µg, 5 µg, or 6 µg total protein.

In some embodiments, the methods further comprise selecting the second sample loading quantity based on MS signals of the second set of peptide products.

In some embodiments, the methods further comprise selecting the first sample loading quantity based on MS signals of the first set of peptide products.

In some embodiments, each of the plurality of sample loading quantities has the same total volume.

In some embodiments, n is 1 or greater or n is 3.

In some embodiments, m is 1 or greater or m is 3.

In some embodiments, the middle set of qualified ions of peptide products of the second polypeptide are selected based on the sequences of each of the peptide products.

In another aspect, the present invention provides methods for detecting a contaminate polypeptide in the production of a therapeutic polypeptide, the method comprising: (a) obtaining a sample comprising the therapeutic polypeptide; (b) determining if the contaminate polypeptide is present in the sample; wherein the presence of the contaminate polypeptide is based on the absolute quantification of the contaminant polypeptide in the sample using the quantification methods provided herein.

In another aspect, the present invention provides systems for absolute quantification of a first polypeptide in a sample comprising the first polypeptide and a second polypeptide, the system comprising: (a) a mass spectrometer; (b) a computer comprising; (c) a non-transitory computer readable medium including instructions stored thereon which, when executed, perform processing including: calculating the average or sum of an MS signal for: (i) a top set of n number of qualified ions of peptide products of the first polypeptide with the highest MS signals at the first sample loading quantity (A); (ii) a top set of n number of qualified ions of peptide products of the second polypeptide with the highest MS signals at the second sample loading quantity (B); (iii) a middle set of m number of qualified ions of peptide products of the second polypeptide at the first sample loading quantity (C); and (iv) the middle set of qualified ions of peptide products of the second polypeptide at the second sample loading quantity (D), wherein A, B, C, and D are all calculated using the average or all calculated using the sum of the MS signal; and determining an absolute quantity of the first polypeptide in the first sample loading quantity based on the following formula:

[(A)/(C)]*(mole of the second polypeptide at the first loading quantity)*[(D)/(B)], or mathematical equivalents thereof. In some embodiments, the systems further comprise a liquid chromatograph.

In another aspect, the present invention provides non-transitory computer readable mediums including instructions stored thereon which, when executed, perform processing for absolute quantification of a first polypeptide in a sample comprising the first polypeptide and a second polypeptide, the processing including: calculating the average or sum of an MS signal for: (i) a top set of n number of qualified ions of peptide products of the first polypeptide with the highest MS signals at the first sample loading quantity (A); (ii) a top set of n number of qualified ions of peptide products of the second polypeptide with the highest MS signals at the second sample loading quantity (B); (iii) a middle set of m number of qualified ions of peptide products of the second polypeptide at the first sample loading quantity (C); and (iv) the middle set of qualified ions of peptide products of the second polypeptide at the second sample loading quantity (D), wherein A, B, C, and D are all calculated using the average or all calculated using the sum of the MS signal; and determining an absolute quantity of the first polypeptide in the first sample loading quantity based on the following formula:

[(A)/(C)]*(mole of the second polypeptide at the first loading quantity)*[(D)/(B)], or mathematical equivalents thereof.

These and other aspects and advantages of the present invention will become apparent from the subsequent detailed description and the appended claims. It is to be understood that one, some, or all of the properties of the various embodiments described herein may be combined to form other embodiments of the present invention.

DETAILED DESCRIPTION OF THE INVENTION

Figure 1:
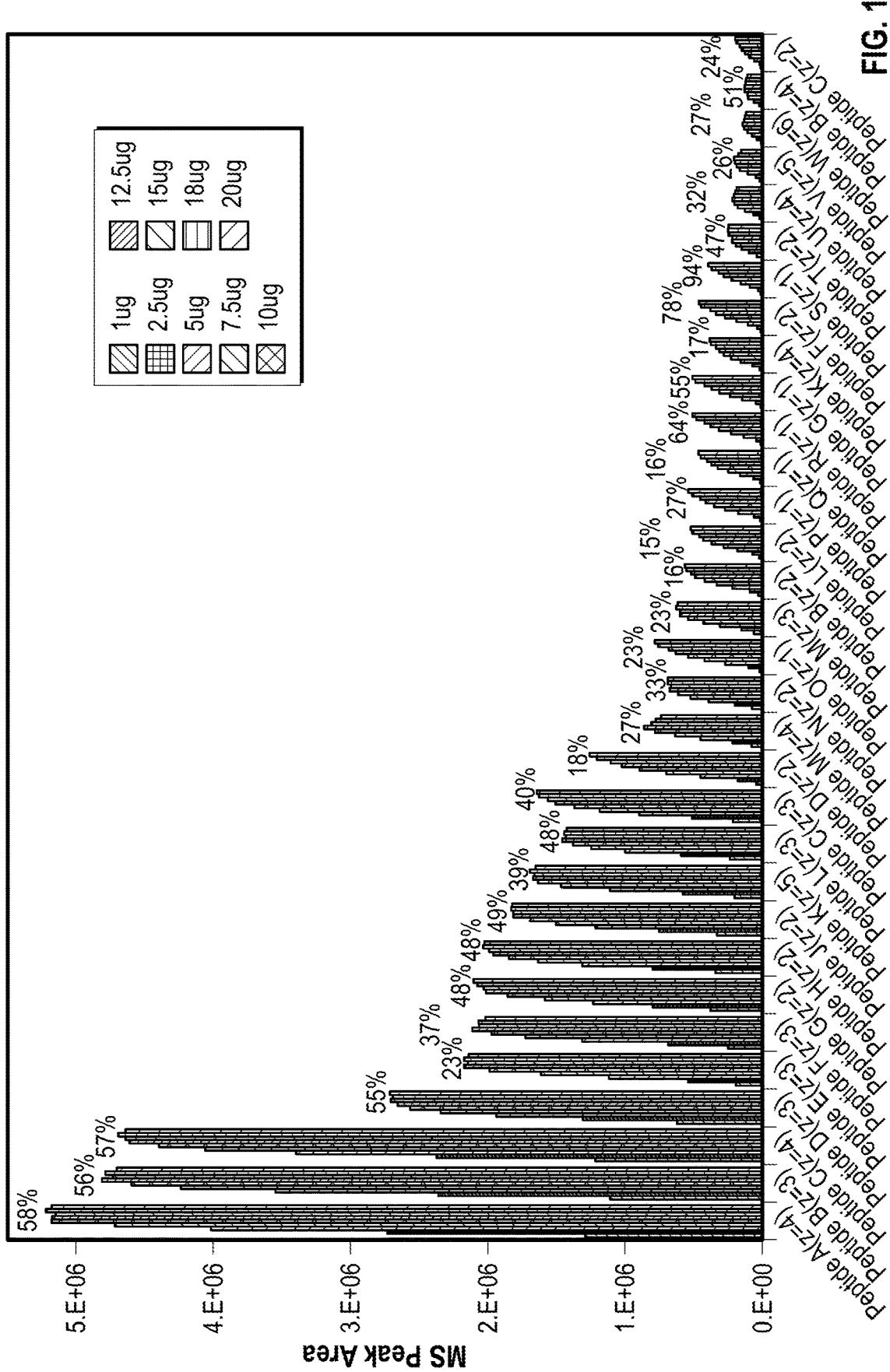
FIG. 1 shows a histogram of MS peak areas for the forty most abundant peptide product ions observed from a LC/MS analysis of a sample comprising sphingomyelin phosphodiesterase (ASM) at different sample loading quantities (the sample loading quantity per LC/MS analysis is ordered as 1 µg, 2.5 µg, 5 µg, 7.5 µg, 10 µg, 12.5 µg, 15 µg, 18 µg, and 20 µg, from left to right for each peptide product bar set). The average percent error for each peptide product ion across the sample loading quantities is shown above the peptide product bar set.

The present invention provides methods for absolute quantification of a first polypeptide in a sample comprising a plurality of polypeptides comprising the first polypeptide and a second polypeptide, the methods comprising determining an absolute quantity of the first polypeptide in the sample based on the average or sum of MS signals for: a top set of n number of qualified ions of peptide products of the first polypeptide with the highest MS signals at the first sample loading quantity (A); a top set of n number of qualified ions of peptide products of the second polypeptide with the highest MS signals at the second sample loading quantity (B); a middle set of m number of qualified ions of peptide products of the second polypeptide at the first sample loading quantity (C); and the middle set of qualified ions of peptide products of the second polypeptide at the second sample loading quantity (D), wherein A, B, C, and D are all calculated using the average or all calculated using the sum of MS signals. In some embodiments, the first polypeptide is less abundant than a second polypeptide in the sample. In some embodiments, the absolute quantity of a first polypeptide is determined by the following formula:

[(A)/(C)]*(mole of the second polypeptide at the first loading quantity)*[(D)/(B)].

The methods of the present invention are also referred to herein as Mid-3. As used herein, "qualified," as used in reference to ions, refers to peptide product ions that are suitable for the quantification methods described herein. In some embodiments, the qualified peptide product ions exclude non-tryptic peptide product ions or peptide product ions with post-translational modifications.

The methods of the present invention described herein provide, for example, improved accuracy and reproducibility of polypeptide quantification over a larger dynamic range of polypeptide concentrations in a sample, as compared to label-free absolute quantification methods known in the art (e.g., Hi-3; J. C. Silva et al., supra). Without wishing to be bound by theory, label-free absolute quantification methods are based on the finding that, assuming an equimolar amount of each of a plurality of polypeptides in a sample, the average MS detector response from the top n most abundant ions of a peptide product of a polypeptide is similar across each of the plurality of polypeptides (i.e., peptide product concentration correlates with detector response). Therefore, the quantity of a polypeptide of unknown concentration may be determined by comparison to a standard polypeptide of known concentration. However, using the most abundant ions of peptide products of a polypeptide standard for absolute quantification may lead to poor accuracy and reproducibility. For example, quantification inaccuracy may arise due to the observation of nonlinear behavior for top ionizing peptide products due to MS detector saturation. Furthermore, such methods may rely on spiking in a known quantity of a standard polypeptide or analyzing a known quantity of a standard protein sample in a LC/MS analysis separate from the sample containing the polypeptide of unknown concentration. Both approaches may lead to a reduction in quantification accuracy and an increase in variability. For example, reproducibly aliquoting a known quantity of a standard polypeptide to any number of samples may be challenging and calibrating a quantification calculation based on a standard polypeptide that is digested in a separate enzymatic reaction from the sample containing the unknown polypeptide may create additional variation in based on the degree of digestion completion.

The present invention provides quantification methods that integrate elements to achieve improved accuracy and reproducibility of polypeptide quantification. First, the absolute quantification methods of the present invention take advantage of polypeptide sample systems comprising a polypeptide with a known concentration and that is in high abundance relative to other polypeptides in the sample (e.g., a therapeutic protein in a manufacturing sample or albumin in a serum sample) and do not require comparison to a spiked-in or separately analyzed standard polypeptide. Second, the absolute quantification methods of the present invention use MS measurements at two concentrations to avoid MS detector saturation of the top n peptide product ions of the high abundant polypeptide. Third, the absolute quantification methods of the present invention further utilize a middle set of peptide product ions with reduced quantification error in comparison to top peptides to reduce overall quantification error. The advantages of the methods of the present invention were demonstrated in a direct comparison to the label-free absolute quantification method known in the art (i.e., Hi-3). For example, as shown in Example 2, across a series of assays and samples the methods disclosed in the present invention achieved a 16% relative standard deviation, whereas the Hi-3 method had an 82% relative standard deviation.

As discussed below in more detail, the present invention provides methods useful for MS-based label-free absolute quantification of low-abundance polypeptides (e.g., a first polypeptide) using information from another polypeptide (e.g., the second polypeptide) that has a known concentration and is higher in relative abundance than the low-abundance polypeptides, the methods including any one or more of the following: (a) performing a loading study to determine two sample loading concentrations at which data is obtained and/or analyzed for quantification of low-abundance polypeptides (e.g., the first sample loading quantity and the second sample loading quantity); (b) selecting qualified peptide product ions for polypeptide quantification (e.g., a top set of n number of qualified ions of peptide products of the first polypeptide, a top set of n number of qualified ions of peptide products of the second polypeptide, and a middle set of m number of qualified ions of peptide products of the second polypeptide); and (c) determining absolute polypeptide quantity of a low-abundance polypeptide using MS signals (e.g., MS signals from peptide products of the first polypeptide and the second polypeptide).

Performing a Loading Study to Determine a First Sample Loading Quantity and a Second Sample Loading Quantity The present invention provides methods for performing a loading study of a sample over the desired dynamic range of the assay. The MS signal information obtained from the loading study allows for, for example, selection of a first sample loading quantity wherein the peptide products of the first polypeptide are detectable (the first polypeptide is in low abundance relative to the second polypeptide), selection of a second sample loading quantity wherein the top n number of qualified highest abundant peptide product ions of the second polypeptide do not saturate the MS detector, and selection of a first sample loading quantity and a second sample loading quantity wherein a middle set of m number of qualified ions of peptide products of the second polypeptide demonstrate reduced quantification error (i.e., increased linear behavior relative to the most abundant peptide product ions).

In some embodiments, the methods comprise analyzing peptide products of a plurality of polypeptides at a plurality of sample loading quantities using a liquid chromatography/mass spectrometry (LC/MS) technique to obtain MS signals of ions of the peptide products of the plurality of polypeptides at each of the plurality of sample loading quantities, wherein the plurality of sample loading quantities comprises a first sample loading quantity and a second sample loading quantity, and wherein the first sample loading quantity is greater than the second sample loading quantity. In some embodiments, the MS signal is ionization intensity. In some embodiments, the MS signal is peak height. In some embodiments, the MS signal is peak area. In some embodiments, the MS signal is peak volume.

In some embodiments, information obtained from a loading study may be applied to subsequent sample analyses for the quantification of a polypeptide (e.g., selecting 2 sample loading quantities for additional sample analyses via an LC/MS technique).

In some embodiments, the plurality of sample loading quantities comprises at least 2 sample loading quantities. In some embodiments, the plurality of sample loading quantities comprises 2, 3, 4, 5, 6, 7, 8, 9, 10, 11, 12, 13, 14, or 15 sample loading quantities.

Sample loading quantities may vary depending on the LC/MS instrumentation used (e.g., based on the loading capacity of a chromatography column). In some embodiments, the plurality of sample loading quantities comprises sample loading quantities in the range of about 0.1 µg to about 100 about 0.1 µg to about 75 µg, about 0.1 µg to about 50 µg, about 0.1 µg to about 40 µg, about 0.1 µg to about 30 µg, about 0.1 µg to about 20 µg, about 0.1 µg to about 15 µg, about 0.1 µg to about 10 µg, about 1 µg to about 30 µg, about 1 µg to about 20 µg, about 1 µg to about 15 µg, or about 1 µg to about 10 µg.

In some embodiments, the sample loading quantity is about 0.5 µg, about 1 µg, about 1.5 µg, about 2 µg, about 2.5 µg, about 3 µg, about 3.5 µg, about 4 µg, about 4.5 µg, about 5 µg, about 5.5 µg, about 6 µg, about 6.5 µg, about 7 µg, about 7.5 µg, about 8 µg, about 8.5 µg, about 9 µg, about 9.5 µg, about 10 µg, about 10.5 µg, about 11 µg, about 11.5 µg, about 12 µg, about 12.5 µg, about 13 µg, about 13.5 µg, about 14 µg, about 14.5 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, or about 30 µg.

In some embodiments, the plurality of sample loading quantities comprises a first sample loading quantity and a second sample loading quantity, wherein the first sample loading quantity is about 10 µg, and wherein the second sample loading quantity is about 0.5 µg to 10 µg, or 3 µg to 6 µg, or 1 µg, 2 µg, 3 µg, 4 µg, 5 µg, or 6 µg.

In some embodiments, the first sample loading quantity is selected based on MS signals of peptide products of the first polypeptide. In some embodiments, the first sample loading quantity is selected based on MS signals of peptide products of the second polypeptide. In some embodiments, the first sample loading quantity is selected based on MS signals of peptide products of the first polypeptide and MS signals of peptide products of the second polypeptide.

In some embodiments, the second sample loading quantity is selected based on MS signals of peptide products of the second polypeptide.

In some embodiments, subsequent sample loading quantities analyzed in a loading study are based on data from a previously analyzed sample loading quantity.

The volume of each sample loading quantity may vary depending on the LC/MS instrumentation used (e.g., based on the size of the sample loop). In some embodiments, each of the plurality of sample loading quantities has the same total volume. In some embodiments, the volume of each of a plurality of sample loading quantities is about 1 µL to about 60 µL, about 10 µL to about 60 µL, about 20 µL to about 50 µL, or about 30 µL to about 50 µL. In some embodiments, the volume of each of a plurality of sample loading quantities is the same and is about 1 µL to about 60 µL, about 10 µL to about 60 µL, about 20 µL to about 50 µL, or about 30 µL to about 50 µL. In some embodiments, the volume of each of a plurality of sample loading quantities is about 5 µL, 10 µL, 15 µL, 20 µL, 25 µL, 30 µL, 35 µL, 40 µL, 45 µL, 50 µL, 55 µL, or 60 µL.

Selecting Qualified Peptide Product Ions of the First Polypeptide and the Second Polypeptide The present invention provides methods for selecting sets of qualified ions of peptide products for absolute quantification of a first polypeptide in a sample comprising a plurality of polypeptides comprising the first polypeptide and a second polypeptide, wherein the first polypeptide is in lower abundance relative to the second polypeptide. For example, the invention provides methods for selection of any one of: a top set of n number of qualified ions of peptide products of the first polypeptide, a top set of n number of qualified ions of peptide products of the second polypeptide, and a middle set of m number of qualified ions of peptide products of the second polypeptide.

In some embodiments, the methods of the present invention comprise selecting a top set of n number of qualified ions of peptide products of the first polypeptide with the highest MS signal at the first sample loading quantity.

In some embodiments, the methods of the present invention comprise selecting a top set of n number of qualified ions of peptide products of the second polypeptide with the highest MS signals at the second sample loading quantity.

The number of MS identifiable peptide products of a polypeptide may vary depending on concentration and characteristics of the polypeptide. In some embodiments, the concentration and characteristics of the first polypeptide may result in identification of a limited number of peptide products at the first sample loading quantity. In some embodiments, n is 1 or greater, wherein n is an integer. In some embodiments, n is 3. In some embodiments, n is 1, 2, 3, 4, 5, 6, 7, 8, 9, or 10.

In some embodiments, the qualified ions of peptide products with the highest MS signals may exclude peptide product ions with certain characteristics, including, for example, missed enzymatic cleavages, post-translational modifications, and overlapping LC elution profiles and isotope distributions. For example, if a sample is digested with trypsin and the peptide product with the highest MS signal is a non-tryptic peptide product, this peptide product may be excluded from the selection of a top set of n number of qualified ions of peptide products of the first polypeptide or a top set of n number of qualified ions of peptide products of the second polypeptide. In some embodiments, the qualified ions of a peptide product with the highest MS signals may exclude peptide product ions originating from portions of a polypeptide that are not reproducibly present as part of the originating polypeptide (e.g., the peptide product originating from a cleavage product of the polypeptide and thus may not be present in the sample at the same concentration as the originating polypeptide).

In some embodiments, the methods of the present invention comprise selecting a middle set of m number of qualified ions of peptide products of the second polypeptide, wherein the middle set of qualified ions of peptide products of the second polypeptide is selected based on quantification error of the qualified ions of peptide products of the second polypeptide from the plurality of sample loading quantities, or the first sample loading quantity and/or the second sample loading quantity. Generally, each peptide product ion of the middle set of m number of qualified ions of peptide products of the second polypeptide is selected based on having the lowest quantification error relative to the total set of ions of peptide products of the second polypeptide. In some embodiments, each peptide product ion of the middle set of m number of qualified ions of peptide products of the second polypeptide has a lower quantification error than the most abundant peptide product ion of the second polypeptide. In some embodiments, peptide product ions of the middle set of m number of qualified ions of peptide products of a second polypeptide have lower quantification error than a top set of n number of qualified ions of peptide products of the second polypeptide with the highest MS signals.

In some embodiments, the qualified ions of peptide products with the lowest quantification error may exclude peptide product ions with certain characteristics, including, for example, missed enzymatic cleavages, post-translational modifications, and overlapping LC elution profiles and isotope distributions. For example, in some embodiments, if a sample is digested with trypsin and the peptide product with the lowest quantification error is a non-tryptic peptide product, this peptide product may be excluded from the selection of a middle set of m number of qualified ions of peptide products of the second polypeptide. In some embodiments, the qualified ions of a peptide product with the highest MS signals may exclude peptide product ions originating from portions of a polypeptide that are not reproducibly present as part of the originating polypeptide (e.g., the peptide product originating from a cleavage product of the polypeptide and thus may not be present in the sample at the same concentration as the originating polypeptide).

In some embodiments, selection of a middle set of m number of qualified ions of peptide products of the second polypeptide is based on quantification error obtained from a loading study. In some embodiments, selection of a middle set of m number of qualified ions of peptide products of the second polypeptide is based on quantification error obtained from a plurality of sample loading quantities. In some embodiments, quantification error is an average percent error of a plurality of sample loading quantities. In some embodiments, selection of a middle set of m number of qualified ions of peptide products of the second polypeptide is based on quantification error obtained from a first sample loading quantity. In some embodiments, selection of a middle set of m number of qualified ions of peptide products of the second polypeptide is based on quantification error obtained from a second sample loading quantity. In some embodiments, selection of a middle set of m number of qualified ions of peptide products of the second polypeptide is based on quantification error obtained from a first sample loading quantity and a second sample loading quantity.

In some embodiments, m is 1 or greater, wherein m is an integer. In some embodiments, m is 3. In some embodiments, m is 1, 2, 3, 4, 5, 6, 7, 8, 9, or 10.

In some embodiments, n is equal to m. In some embodiments, n is not equal to m. In some embodiments, n and m are 2 or greater, wherein n and m are an integer. In some embodiments, n and m are 3.

In some embodiments, each of the top set of qualified ions of peptide products of a second polypeptide is different than each of a middle set of qualified ions of peptide products of the second polypeptide. In some embodiments, a qualified peptide product ion is a member of a top set of qualified ions of peptide products of a second polypeptide and a middle set of qualified ions of peptide products of the second polypeptide.

In some embodiment, the qualified peptide product ion comprises a carbamidomethylated cysteine. In some embodiment, the qualified peptide product ion comprises a carboxymethylated cysteine.

Determining Absolute Polypeptide Quantity of Low-Abundance Polypeptides

The present invention provides methods for calculating the absolute polypeptide quantity of a first polypeptide in a sample comprising a plurality of polypeptides comprising the first polypeptide and a second polypeptide, the methods comprising determining an absolute quantity of the first polypeptide in the sample based on the average or sum of MS signals for: a top set of n number of qualified ions of peptide products of the first polypeptide with the highest MS signals at the first sample loading quantity (A); a top set of n number of qualified ions of peptide products of the second polypeptide with the highest MS signals at the second sample loading quantity (B); a middle set of m number of qualified ions of peptide products of the second polypeptide at the first sample loading quantity (C); and the middle set of qualified ions of peptide products of the second polypeptide at the second sample loading quantity (D), wherein A, B, C, and D are all calculated using the average or all calculated using the sum of MS signals.

In some embodiments, the absolute quantity of a first polypeptide is determined based on the following formula:

$$[(A)/(C)]*(\text{mole of the second polypeptide at the first loading quantity})*[(D)/(B)],$$

or mathematical equivalents thereof.

In some embodiments, A, B, C, and D are all calculated using the average of MS signals. In some embodiments, A, B, C, and D are all calculated using the sum of MS signals.

In some embodiments, the MS signal is ionization intensity. In some embodiments, the MS signal is peak height. In some embodiments, the MS signal is peak area. In some embodiments, the MS signal is peak volume.

In some embodiments, the top set of n number of qualified ions of peptide products of a first polypeptide with the highest MS signals is predetermined. In some embodiments, the top set of n number of qualified ions of peptide products of a second polypeptide with the highest MS signals is predetermined. In some embodiments, the middle set of m number of qualified ions of peptide products of a second polypeptide is predetermined. In some embodiments, the ratio of a top set of n number of qualified ions of peptide products of a second polypeptide with the highest MS signals at a second sample loading quantity (B) and a middle set of qualified ions of peptide products of the second polypeptide at the second sample loading quantity (D) is predetermined.

In some embodiments, the average or sum of MS signals for: a top set of n number of qualified ions of peptide products of the first polypeptide with the highest MS signals at the first sample loading quantity (A); a top set of n number of qualified ions of peptide products of the second polypeptide with the highest MS signals at the second sample loading quantity (B); a middle set of m number of qualified ions of peptide products of the second polypeptide at the first sample loading quantity (C); and the middle set of qualified ions of peptide products of the second polypeptide at the second sample loading quantity (D), are determined from 2 LC/MS analyses of the sample. In some embodiments, additional replicates analyses of the 2 LC/MS analyses are performed.

In some embodiments, the average or sum of MS signals for: a top set of n number of qualified ions of peptide products of the first polypeptide with the highest MS signals at the first sample loading quantity (A); a top set of n number of qualified ions of peptide products of the second polypeptide with the highest MS signals at the second sample loading quantity (B); a middle set of m number of qualified ions of peptide products of the second polypeptide at the first sample loading quantity (C); and the middle set of qualified ions of peptide products of the second polypeptide at the second sample loading quantity (D), are determined from 2 LC/MS analyses of the sample, wherein the LC/MS analyses are not part of the loading study. In some embodiments, additional replicates analyses of the 2 LC/MS analyses are performed.

In some embodiments, the quantification method comprises MS signals from two or more polypeptides of known quantity.

In some embodiments, the methods further comprise determining the absolute quantity of a second polypeptide. Methods for determining protein quantity of a second polypeptide include, for example, ELISA and Western blot.

It is contemplated that more than one polypeptide of unknown concentration per assay can be identified and quantified using the methods of the present invention. For example, from the equation disclosed above, the top set of n number of qualified ions of peptide products of the first polypeptide with the highest MS signals at the first sample loading quantity (A) can be substituted with a top set of n number of qualified ions of peptide products of another polypeptide with the highest MS signals at the first sample loading quantity to calculate the quantity of the other polypeptide.

Samples and Sample Preparation

The methods of the present invention are useful for absolute quantification of a first polypeptide in a sample comprising a plurality of polypeptides comprising the first polypeptide and a second polypeptide, wherein the first polypeptide is in lower abundance relative to the second polypeptide.

In some embodiments, the first polypeptide is at least about 10-fold lower in abundance than a second polypeptide. In some embodiments, the first polypeptide is at least about 100-fold lower in abundance than a second polypeptide. In some embodiments, the first polypeptide is at least about 1000-fold lower in abundance than a second polypeptide. In some embodiments, the first polypeptide is at least about 2-fold to about $1 \times 10^9$-fold lower in abundance than a second polypeptide. For example, the first polypeptide is measured at a quantity of one part per billion.

In some embodiments, the second polypeptide is at least about 10-fold greater in abundance than a first polypeptide. In some embodiments, the second polypeptide is at least about 100-fold greater in abundance than a first polypeptide. In some embodiments, the second polypeptide is at least about 1000-fold greater or $1 \times 10^9$-fold greater in abundance than a first polypeptide. In some embodiments, the second polypeptide is at least about 2-fold to about $1 \times 10^9$-fold higher in abundance than a first polypeptide.

Sample preparation techniques necessary to produce peptide products of a plurality of polypeptides in a sample for analysis via LC/MS techniques are known in the art.

In some embodiments, the peptide products of a plurality of polypeptides in a sample are obtained via sample digestion prior to analyzing the peptide products using an LC/MS technique. In some embodiments, sample digestion comprises enzymatic digestion using a protease. In some embodiments, the enzymatic digestion is performed using one or more of trypsin, Lys-C, IdeS, IdeZ, PNGase F, thermolysin, pepsin, elastase, Arg-C, TEV, Glu-C, Asp-N, and Factor Xa. In some embodiments, the peptide products of a plurality of polypeptides in a sample are tryptic peptide products.

In some embodiments, sample digestion comprises chemical digestion, such as acid hydrolysis.

In some embodiments, the methods comprise obtaining a sample. Techniques for obtaining samples for LC/MS analysis are known in the art and include, for example, tissue (e.g., blood, plasma) collection and cell culture.

In some embodiments, the sample has been purified or enriched. In some embodiments, the methods comprise processing the plurality of polypeptides in a sample to produce peptide products. In some embodiments, processing the plurality of polypeptides in a sample comprises one or more of: (a) centrifuging the sample to isolate the plurality of polypeptides; (b) purifying the plurality of polypeptides in the sample; (c) removing from the sample components incompatible with subsequent processing and LC/MS analysis; (d) digesting the plurality of polypeptides to produce the peptide products; and (e) purifying the peptide products prior to LC/MS analysis.

In some embodiments, the first polypeptide is a host cell protein. In some embodiments, the second polypeptide is a recombinant polypeptide produced by a host cell. In some embodiments, the second polypeptide is a therapeutic polypeptide, such as an antibody (e.g., a recombinant antibody), or an enzyme (e.g., a recombinant enzyme), or a peptide (e.g., an insulin). In some embodiments, the second polypeptide is viral protein, such as a capsid of a viral particle (e.g., such as for a gene therapy). In some embodiments, the sample is a cell culture sample. In some embodiments, the sample is a pharmaceutical product or an intermediate thereof.

In some embodiments, the first polypeptide is a biomarker, such a circulating biomarker. In some embodiments, the second polypeptide is serum albumin. In some embodiments, the sample is a blood or serum sample.

Liquid Chromatography/Mass Spectrometry (LC/MS) Techniques

The present invention contemplates a diverse array of LC/MS techniques for generating tandem mass spectra of a sample comprising a plurality of polypeptides comprising the first polypeptide and a second polypeptide.

In some embodiments, the LC/MS technique comprises separating the peptide products via a liquid chromatography technique. Liquid chromatography techniques contemplated by the present application include methods for separating polypeptides and liquid chromatography techniques compatible with mass spectrometry techniques. In some embodiments, the liquid chromatography technique comprises a high performance liquid chromatography technique. Thus, in some embodiments, the liquid chromatography technique comprises an ultra-high performance liquid chromatography technique. In some embodiments, the liquid chromatography technique comprises a high-flow liquid chromatography technique. In some embodiments, the liquid chromatography technique comprises a low-flow liquid chromatography technique, such as a micro-flow liquid chromatography technique or a nano-flow liquid chromatography technique. In some embodiments, the liquid chromatography technique comprises an online liquid chromatography technique coupled to a mass spectrometer. In some embodiments, the online liquid chromatography technique is a high performance liquid chromatography technique. In some embodiments, the online liquid chromatography technique is an ultra-high performance liquid chromatography technique.

In some embodiments, capillary electrophoresis (CE) techniques, or electrospray or MALDI techniques may be used to introduce the sample to the mass spectrometer.

In some embodiment, the mass spectrometry technique comprises an ionization technique. Ionization techniques contemplated by the present application include techniques capable of charging polypeptides and peptide products. Thus, in some embodiments, the ionization technique is electrospray ionization. In some embodiments, the ionization technique is nanoelectrospray ionization. In some embodiments, the ionization technique is atmospheric pressure chemical ionization. In some embodiments, the ionization technique is atmospheric pressure photoionizationionization. In some embodiments, the ionization technique is matrix-assisted laser desorption ionization (MALDI). In some embodiment, the mass spectrometry technique comprises electrospray ionization, nanoelectrospray ionization, or a matrix-assisted laser desorption ionization (MALDI) technique.

In some embodiments, the LC/MS technique comprises analyzing the peptide products via a mass spectrometry technique. Mass spectrometers contemplated by the present invention, to which an online liquid chromatography technique is coupled, include high-resolution mass spectrometers and low-resolution mass spectrometers. Thus, in some embodiments, the mass spectrometer is a time-of-flight (TOF) mass spectrometer. In some embodiments, the mass spectrometer is a quadrupole time-of-flight (Q-TOF) mass spectrometer. In some embodiments, the mass spectrometer is a quadrupole ion trap time-of-flight (QIT-TOF) mass spectrometer. In some embodiments, the mass spectrometer is an ion trap. In some embodiments, the mass spectrometer is a single quadrupole. In some embodiments, the mass spectrometer is a triple quadrupole (QQQ). In some embodiments, the mass spectrometer is an orbitrap. In some embodiments, the mass spectrometer is a quadrupole orbitrap. In some embodiments, the mass spectrometer is a fourier transform ion cyclotron resonance (FT) mass spectrometer. In some embodiments, the mass spectrometer is a quadrupole fourier transform ion cyclotron resonance (Q-FT) mass spectrometer. In some embodiments, the mass spectrometry technique comprises positive ion mode. In some embodiments, the mass spectrometry technique comprises negative ion mode. In some embodiments, the mass spectrometry technique comprises a time-of-flight (TOF) mass spectrometry technique. In some embodiments, the mass spectrometry technique comprises a quadrupole time-of-flight (Q-TOF) mass spectrometry technique. In some embodiments, the mass spectrometry technique comprises an ion mobility mass spectrometry technique. In some embodiments a low-resolution mass spectrometry technique, such as an ion trap, or single or triple-quadrupole approach is appropriate.

In some embodiments, the LC/MS technique comprises processing the obtained MS signals of the peptide products. In some embodiments, the LC/MS technique comprises peak detection. In some embodiments, the LC/MS technique comprises determining ionization intensity of a peptide product. In some embodiments, the LC/MS technique comprises determining peak height of a peptide product. In some embodiments, the LC/MS technique comprises determining peak area of a peptide product. In some embodiments, the LC/MS technique comprises determining peak volume of a peptide product. In some embodiments, the LC/MS technique comprises identifying the peptide products by amino acid sequence. In some embodiments, the LC/MS technique comprises manually validating the peptide product amino acid sequence assignments. In some embodiments, the LC/MS technique comprises identifying the first polypeptide by a protein identifier. In some embodiments, the LC/MS technique comprises identifying one or more of the plurality of polypeptides by a protein identifier, which may be identified in a database search or a library search.

In some embodiments, identification of peptide products of a polypeptide can be achieved using spectral libraries. Generally, use of spectral libraries allows for the imputation of knowledge gained regarding a polypeptide system and results in increased speed of data analysis and decreased error.

Use of Absolute Quantification Methods

The MS-based label-free absolute quantification methods disclosed herein are especially suited for uses comprising quantification of a low-abundance polypeptide in a sample comprising the low-abundance polypeptide and another polypeptide of relative high-abundance. The MS-based label-free absolute quantification methods disclosed herein may, e.g., constitute a single step in a multi-step process, such as quantification of a low-abundance protein in the purification of a therapeutic protein.

In some embodiments, the present invention provides methods of detecting a contaminate polypeptide in the production of a therapeutic polypeptide, the methods comprising: (a) obtaining a sample comprising the therapeutic polypeptide; (b) determining if the contaminate polypeptide is present in the sample, wherein the presence of the contaminate polypeptide is based on the absolute quantification of the contaminate polypeptide in the sample using the methods disclosed herein. In some embodiments, the contaminate polypeptide is a host cell protein. In some embodiments, the contaminate polypeptide is a viral protein, such as a capsid protein. In some embodiments, the second polypeptide is a therapeutic polypeptide. In some embodiments, more than one contaminate polypeptide is detected in a sample (e.g., and the total amount of contaminate polypeptides in the sample is quantified). In one embodiment, the sample is taken at various steps during the production process of a recombinant polypeptide (e.g., a therapeutic polypeptide), to assay for purity of the recombinant polypeptide at the various steps. The lower the amount of contaminate polypeptides (e.g., host cell polypeptides) identified, will indicate the higher the purity of the recombinant polypeptide.

In some embodiments, the present invention provides methods of producing a therapeutic polypeptide, the methods comprising: (a) obtaining a sample comprising the therapeutic polypeptide from a stage of the production process, e.g., cell culture harvest or a purification step; (b) identifying a contaminate polypeptide in the sample; (c) determining the level of the contaminate polypeptide in the sample, wherein the level of the contaminate polypeptide is based on the absolute quantification of the contaminate polypeptide in the sample using the methods disclosed herein. In some embodiments, the contaminate polypeptide is a host cell protein. In some embodiments, the contaminate polypeptide is a viral protein, such as a capsid protein. In some embodiments, the second polypeptide is a therapeutic polypeptide. In some embodiments, more than one contaminate polypeptide is detected in a sample (e.g., and the total amount of contaminate polypeptides in the sample is quantified). In one embodiment, the sample is taken at various steps during the production process of a recombinant polypeptide (e.g., a therapeutic polypeptide), to assay for purity of the recombinant polypeptide at the various steps. The lower the amount of contaminate polypeptides (e.g., host cell polypeptides) identified, will indicate the higher the purity of the recombinant polypeptide.

In some embodiments, the present invention provides methods of purifying a therapeutic polypeptide, the methods comprising: (a) obtaining a sample comprising the therapeutic polypeptide from one or more stages of a purification process, e.g., cell culture harvest or a purification step; (b) identifying a contaminate polypeptide in the sample; (c) determining the level of the contaminate polypeptide in the sample at the one or more stages of a purification process, wherein the level of the contaminate polypeptide is based on the absolute quantification of the contaminate polypeptide in the sample using the methods disclosed herein. In some embodiments, the contaminate polypeptide is a host cell protein. In some embodiments, the contaminate polypeptide is a viral protein, such as a capsid protein. In some embodiments, the second polypeptide is a therapeutic polypeptide. In some embodiments, more than one contaminate polypeptide is detected in a sample (e.g., and the total amount of contaminate polypeptides in the sample is quantified). In one embodiment, the sample is taken at various steps during the production process of a recombinant polypeptide (e.g., a therapeutic polypeptide), to assay for purity of the recombinant polypeptide at the various steps. The lower the amount of contaminate polypeptides (e.g., host cell polypeptides) identified, will indicate the higher the purity of the recombinant polypeptide.

In some embodiments, the present invention provides methods of detecting a contaminate polypeptide in a gene therapy product. The methods include for example, (a) obtaining a sample comprising a gene therapy vector, from one or more stages of a purification process, e.g., cell culture harvest or a purification step; (b) identifying a contaminate polypeptide in the sample; (c) determining the level of the contaminate polypeptide in the sample at the one or more stages of a purification process, wherein the level of the contaminate polypeptide is based on the absolute quantification of the contaminate polypeptide in the sample using the methods disclosed herein. In some embodiments, the gene therapy product is associated with a viral protein, such as a capsid. In some embodiments, the gene therapy product comprises a viral protein, such as a capsid. In some embodiments, the gene therapy vector is associated with a viral protein, such as a capsid. In some embodiments, the gene therapy vector is part of a viral particle comprising a viral protein, such as a capsid. In some embodiments, the contaminate polypeptide is a host cell protein. In some embodiments, the contaminate polypeptide is a viral protein, such as a capsid protein. In some embodiments, the contaminate polypeptide is a viral protein that is not associated with the gene therapy product. In some embodiments, the contaminate polypeptide is a viral protein that is not a part of the gene therapy product. In some embodiments, the contaminate polypeptide is a helper virus protein. In some embodiments, the second polypeptide is a viral protein, such as a capsid protein. In some embodiments, more than one contaminate polypeptide is detected in a sample (e.g., and the total amount of contaminate polypeptides in the sample is quantified). In one embodiment, the sample is taken at various steps during the production process of the gene therapy product, to assay for purity of the gene therapy product at the various steps. The lower the amount of contaminate polypeptides (e.g., host cell polypeptides) identified, will indicate the higher the purity of the gene therapy product.

In some embodiments, the present invention provides methods of producing a gene therapy product. The methods include for example, (a) obtaining a sample comprising a gene therapy vector, from one or more stages of a purification process, e.g., cell culture harvest or a purification step; (b) identifying a contaminate polypeptide in the sample; (c) determining the level of the contaminate polypeptide in the sample at the one or more stages of a purification process, wherein the level of the contaminate polypeptide is based on the absolute quantification of the contaminate polypeptide in the sample using the methods disclosed herein. In some embodiments, the gene therapy product is associated with a viral protein, such as a capsid. In some embodiments, the gene therapy product comprises a viral protein, such as a capsid. In some embodiments, the gene therapy vector is associated with a viral protein, such as a capsid. In some embodiments, the gene therapy vector is part of a viral particle comprising a viral protein, such as a capsid. In some embodiments, the contaminate polypeptide is a host cell protein. In some embodiments, the contaminate polypeptide is a viral protein, such as a capsid protein. In some embodiments, the contaminate polypeptide is a viral protein that is not associated with the gene therapy product. In some embodiments, the contaminate polypeptide is a viral protein that is not a part of the gene therapy product. In some embodiments, the contaminate polypeptide is a helper virus protein. In some embodiments, the second polypeptide is a viral protein, such as a capsid protein. In some embodiments, more than one contaminate polypeptide is detected in a sample (e.g., and the total amount of contaminate polypeptides in the sample is quantified). In one embodiment, the sample is taken at various steps during the production process of the gene therapy product, to assay for purity of the gene therapy product at the various steps. The lower the amount of contaminate polypeptides (e.g., host cell polypeptides) identified, will indicate the higher the purity of the gene therapy product.

In some embodiments, the present invention provides methods of purifying a gene therapy product. The methods include for example, (a) obtaining a sample comprising a gene therapy vector, from one or more stages of a purification process, e.g., cell culture harvest or a purification step; (b) identifying a contaminate polypeptide in the sample; (c) determining the level of the contaminate polypeptide in the sample at the one or more stages of a purification process, wherein the level of the contaminate polypeptide is based on the absolute quantification of the contaminate polypeptide in the sample using the methods disclosed herein. In some embodiments, the gene therapy product is associated with a viral protein, such as a capsid. In some embodiments, the gene therapy product comprises a viral protein, such as a capsid. In some embodiments, the gene therapy vector is associated with a viral protein, such as a capsid. In some embodiments, the gene therapy vector is part of a viral particle comprising a viral protein, such as a capsid. In some embodiments, the contaminate polypeptide is a host cell protein. In some embodiments, the contaminate polypeptide is a viral protein, such as a capsid protein. In some embodiments, the contaminate polypeptide is a viral protein that is not associated with the gene therapy product. In some embodiments, the contaminate polypeptide is a viral protein that is not a part of the gene therapy product. In some embodiments, the contaminate polypeptide is a helper virus protein. In some embodiments, the second polypeptide is a viral protein, such as a capsid protein. In some embodiments, more than one contaminate polypeptide is detected in a sample (e.g., and the total amount of contaminate polypeptides in the sample is quantified). In one embodiment, the sample is taken at various steps during the production process of the gene therapy product, to assay for purity of the gene therapy product at the various steps. The lower the amount of contaminate polypeptides (e.g., host cell polypeptides) identified, will indicate the higher the purity of the gene therapy product.

In some embodiments, the methods disclosed herein further comprise adjusting a protocol based on the presence of a contaminant polypeptide. For example, a purification process can be adjusted based on the presence of an identified and quantified contaminant polypeptide. Such adjustments provide methods for improving purity of a target polypeptide, such as a therapeutic polypeptide.

In some embodiments, the present invention provides methods of treating a disease in an individual, wherein the individual is selected for treatment based on an amount of a biomarker in the individual. In some embodiments, the biomarker is quantified in a serum sample. In some embodiments, the first polypeptide is a biomarker. In some embodiments, the second polypeptide is serum albumin.

In some embodiments, the present invention provides methods of assessing a disease in an individual, wherein the individual is assessed based on an amount of a biomarker in the individual. In some embodiments, the amount of the biomarker is quantified in a serum sample. In some embodiments, the first polypeptide is a biomarker. In some embodiments, the second polypeptide is serum albumin.

In some embodiments, the present invention provides methods of diagnosing a disease in an individual, wherein the individual is diagnosed with the disease based on an amount of a biomarker in the individual. In some embodiments, the amount of the biomarker is quantified in a serum sample. In some embodiments, the first polypeptide is a biomarker. In some embodiments, the second polypeptide is serum albumin.

Systems

The present invention provides systems and non-transitory computer readable mediums useful for determining the absolute polypeptide quantity of a first polypeptide in a sample comprising a plurality of polypeptides comprising the first polypeptide and a second polypeptide.

In some embodiments, the present invention provides a system for absolute quantification of a first polypeptide in a sample comprising the first polypeptide and a second polypeptide, the system comprising: (a) a mass spectrometer; (b) a computer comprising; (c) a non-transitory computer readable medium including instructions stored thereon which, when executed, perform processing including: calculating the average or sum of an MS signal for: (i) a top set of n number of qualified ions of peptide products of the first polypeptide with the highest MS signals at the first sample loading quantity (A); (ii) a top set of n number of qualified ions of peptide products of the second polypeptide with the highest MS signals at the second sample loading quantity (B); (iii) a middle set of m number of qualified ions of peptide products of the second polypeptide at the first sample loading quantity (C); and (iv) the middle set of qualified ions of peptide products of the second polypeptide at the second sample loading quantity (D), wherein A, B, C, and D are all calculated using the average or all calculated using the sum of the MS signal; and determining an absolute quantity of the first polypeptide in the first sample loading quantity based on the following formula:

$$[(A)/(C)]*(\text{mole of the second polypeptide at the first loading quantity})*[(D)/(B)],$$

or mathematical equivalents thereof. In some embodiments, the system further comprises a liquid chromatograph.

In some embodiments, the present invention provides a non-transitory computer readable medium including instructions stored thereon which, when executed, perform processing for absolute quantification of a first polypeptide in a sample comprising the first polypeptide and a second polypeptide, the processing including: calculating the average or sum of an MS signal for: (i) a top set of n number of qualified ions of peptide products of the first polypeptide with the highest MS signals at the first sample loading quantity (A); (ii) a top set of n number of qualified ions of peptide products of the second polypeptide with the highest MS signals at the second sample loading quantity (B); (iii) a middle set of m number of qualified ions of peptide products of the second polypeptide at the first sample loading quantity (C); and (iv) the middle set of qualified ions of peptide products of the second polypeptide at the second sample loading quantity (D), wherein A, B, C, and D are all calculated using the average or all calculated using the sum of the MS signal; and determining an absolute quantity of the first polypeptide in the first sample loading quantity based on the following formula:

$$[(A)/(C)]*(\text{mole of the second polypeptide at the first loading quantity})*[(D)/(B)],$$

or mathematical equivalents thereof.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

As used herein, the term "polypeptide" refers to a polymer comprising amino acids covalently joined via peptide bonds. In some embodiments, the polypeptide is a protein. In some instances, a protein comprises two or more polypeptides (e.g., a multimeric protein, a homomeric protein, a multiprotein complex). Polypeptides may be further modified with non-amino acid moieties. For example, a polypeptide may further comprise enzymatically-mediated modifications and/or chemical modifications (e.g., acetylation, phosphorylation, ubiquitination, formylation, glycosylation, oxidation). Such modifications may occur, for example, in cell-based environments or as a result of sample processing and/or analysis techniques.

As used herein, the term "peptide product" refers to a polymer comprising two or more amino acids covalently joined via peptide bonds obtained following decomposition processing of a polypeptide. For example, peptide products are obtained following decomposition processing of a polypeptide including chemical digestion (e.g., acid hydrolysis) or enzymatic digestion (e.g., trypsin digestion). In some embodiments, the peptide product is a tryptic peptide. In some embodiments, the peptide product is a terminal fragment of a larger polypeptide. In some embodiments, the peptide product is an internal fragment of a polypeptide.

The term "comprises" is used herein to mean that other components, ingredients, steps, etc. are optionally present. For example, an article "comprising" components A, B, and C can consist of (i.e., contain only) components A, B, and C, or can contain not only components A, B, and C but also one or more other components. It is understood that "comprises" and grammatical equivalents thereof include "consisting of" or "consisting essentially of."

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein and in the appended claims, the singular forms "a," "or," and "the" include plural referents unless the context clearly dictates otherwise.

EXAMPLES

Example 1

Loading Study of ASM Demonstrating the Improved Linear MS Signal Response of a Middle Set of Peptide Product Ions of ASM This example demonstrates a loading study using a sample comprising sphingomyelin phosphodiesterase (ASM) for the selection of a first sample loading quantity and a second loading quantity. Furthermore, this example demonstrates the improved linear MS signal response of a middle set of peptide product ions of ASM as compared to a top set of highest abundant peptide product ions of ASM.

In triplicate, an ASM sample was denatured, reduced, and alkylated prior to digestion with LysC and trypsin. LC/MS analysis was performed on the digested samples at 1 µg, 2.5 µg, 5 µg, 7.5 µg, 10 µg, 12.5 µg, 15 µg, 18 µg, and 20 µg. Chromatography was performed with an ACQUITY UPLC with a 2.1 by 150 mm column packed with CSH130 C18 1.7 µm material. Data were acquired using alternating scans of low and elevated collision energy on a Xevo Q-Tof G2-XS to generate precursor and fragment ion information. MS peak areas and the average percent error for each peptide product ion over the range of sample quantities of the top 40 most abundant peptide product ions of ASM were calculated.

FIG. 1 shows a histogram of MS peak areas for the forty most abundant peptide product ions observed from a LC/MS analysis of a sample comprising sphingomyelin phosphodiesterase (ASM) at different sample loading quantities (the sample loading quantity per LC/MS analysis is ordered as 1 µg, 2.5 µg, 5 µg, 7.5 µg, 10 µg, 12.5 µg, 15 µg, 18 µg, and 20 µg, from left to right for each peptide bar set). The average percent error for each peptide product ion across the sample loading quantities is shown above the peptide bar set.

As shown in FIG. 1, the most intense peptide products of ASM have a higher error relative to all peptide product ions, especially as the total sample quantity increases. The peptides in the middle of the peptide product ion distribution behave more linearly and have a lower error relative to all peptide product ions, even up to total sample loading quantities of 20 µg.

Using data in the loading study, a top set of n number of qualified ions of peptide products of the second polypeptide and a middle set of m number of qualified ions of peptide products of the second polypeptide may be selected. For example, the top set of n number, for example, 3, of qualified ions of peptide products of ASM may include peptide product ions selected from Peptide A (z=4), Peptide B (z=3), and Peptide C (z=4). The middle set of m number, for example, 3, of qualified ions of peptide products of ASM may include peptide product ions selected from Peptide D (z=2), Peptide M (z=4), Peptide 0 (z=1), Peptide M (z=3), Peptide B (z=2), Peptide L (z=2), Peptide P (z=1), and Peptide Q (z=1).

Figure 2:
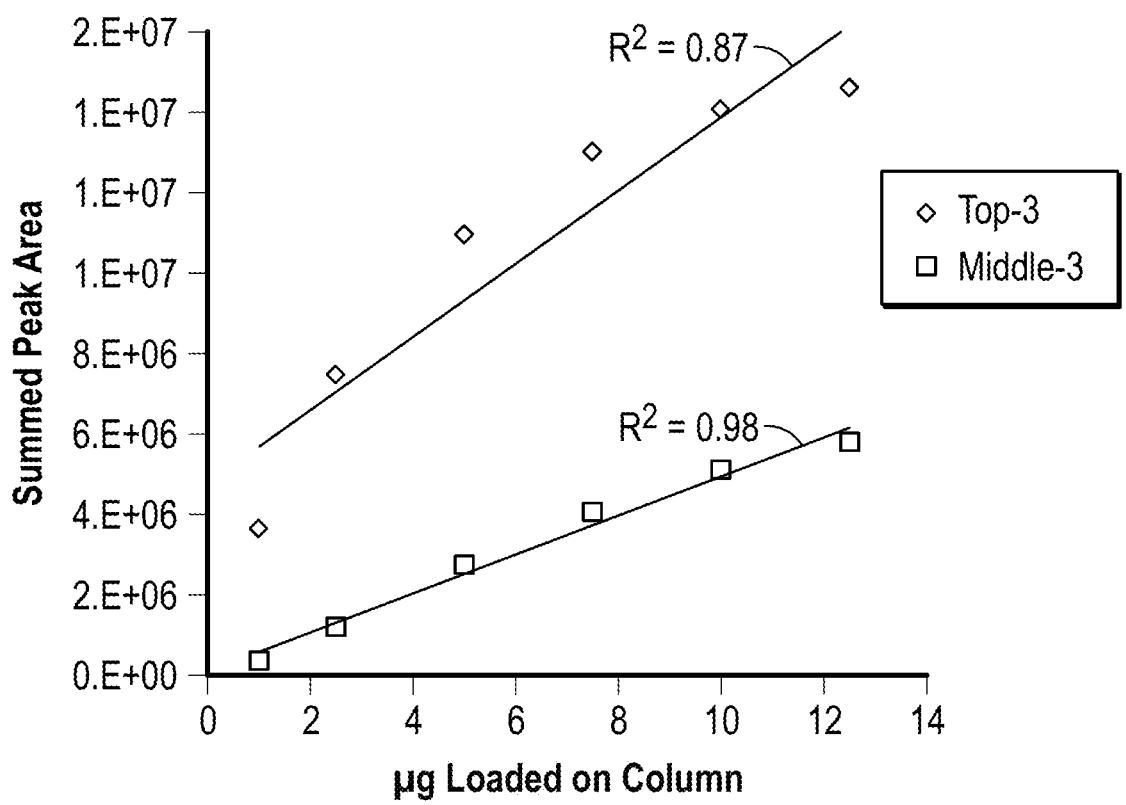
FIG. 2 shows the summed peak area of a middle set of three peptide products (Middle-3; squares) and a top set of three peptide products (Top-3; diamonds) over six concentration points. The $R^2$ for a linear regression of the Middle-3 peptide products is 0.98 and for the Top-3 peptide products is 0.87.

Furthermore, using the data collected from the ASM loading study, the summed peak area versus sample loaded on column (µg) was plotted for each sample loading quantity using the top set of the 3 most abundant peptide product ions (Top-3) and a middle set of 3 peptide product ions (Middle-3) (FIG. 2). The nonlinear behavior of the Top-3 peptide product set can be seen well below the optimal sample loading quantity (10 µg). The Middle-3 peptide product set behaved linearly over the sample loading quantities of the loading study, thus demonstrating that the Middle-3 peptide product ions are suitable for quantification techniques of the present invention. The $R^2$ for a linear regression is also improved using the Middle-3 peptide product set (0.98 for Middle-3 peptide product set compared to 0.87 for Top-3 peptide product set).

The percent error for each peptide product set at each concentration relative to the 2.5 µg load is provided in Table 1. The percent error between the expected ratio and observed ratio for the Middle-3 peptide product set was lower than the Top-3 peptide product set for all sample loading quantities.

TABLE 1

Percent error of the Top-3 peptide product set and Middle-3 peptide product set at each sample loading quantity relative to the 2.5 µg load peptide product set.

| Load (µg) | Hi-3 Error | Mid-3 Error |
| --- | --- | --- |
| 20 | 76% | 33% |
| 18 | 73% | 26% |
| 15 | 68% | 17% |
| 12.5 | 61% | 5% |
| 10 | 53% | 5% |
| 7.5 | 42% | 12% |
| 5 | 27% | 13% |

Example 2

Methods of Determining Quantity for Polypeptides

This example demonstrates the improvement of quantification reproducibility of the Mid-3 method as compared to the Hi-3 method using four protein production lots of a therapeutic protein product assayed on four different occasions.

Four protein production lots (Lot 1, Lot 2, Lot 3, Lot 4) of protein X were prepared and analyzed as disclosed in Example 1. For the Hi-3 method, 200 fmol of a ClpB standard (E. coli Chaperone ClpB) peptide products was spiked in each sample as an internal standard.

Figure 3A:
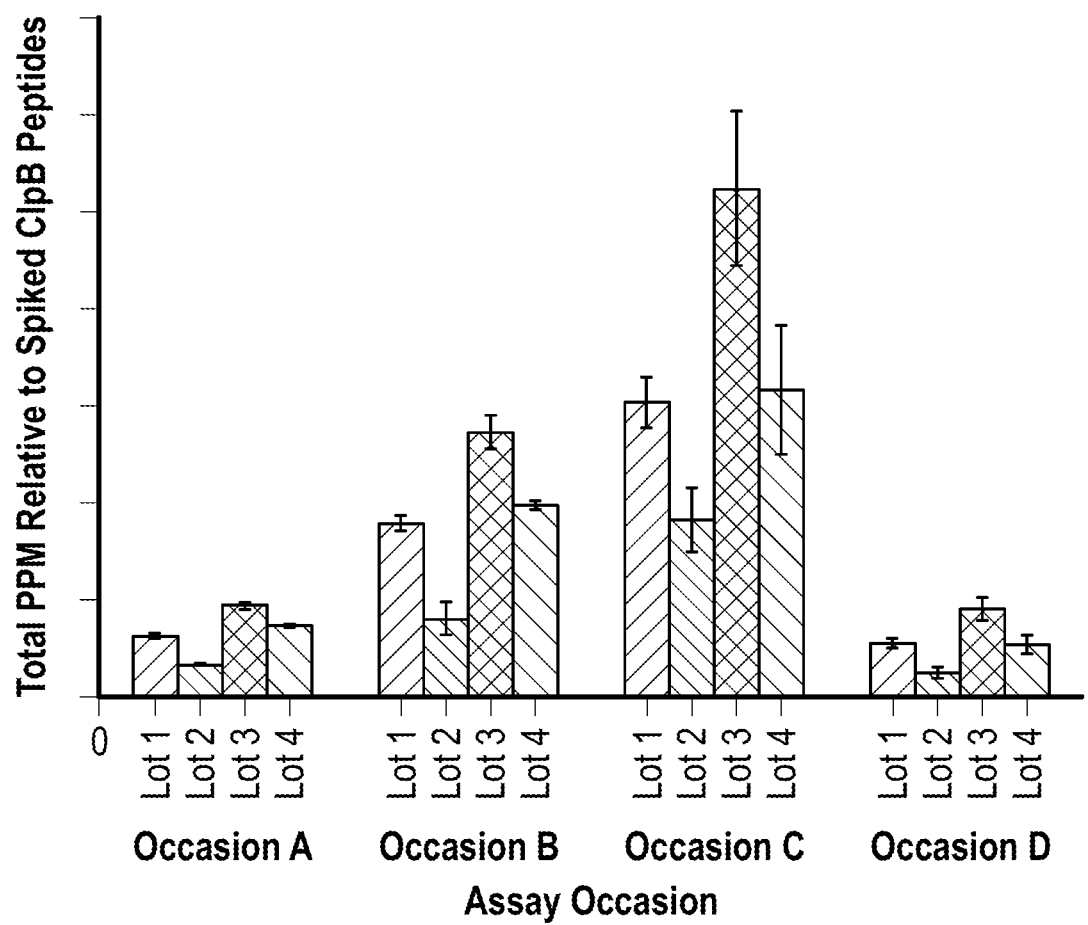
FIGS. 3A-3B show a comparison of the Hi-3 (FIG. 3A) and the Mid-3 (FIG. 3B) quantification methods for four samples (Lot 1, Lot 2, Lot 3, Lot 4, from left to right for each bar set) at four different assay occasions (Occasion A, Occasion B, Occasion C, Occasion D). There was an 82% relative standard deviation for the Hi-3 method (FIG. 3A) and a 16% relative standard deviation for the Mid-3 method (FIG. 3B).

As measured by the Hi-3 method, the total ppm of host cell protein relative to the spiked ClpB peptide products was plotted for each protein production lot (FIG. 3A). The quantification measurements of the Hi-3 method have 82% relative standard deviation.

Figure 3B:
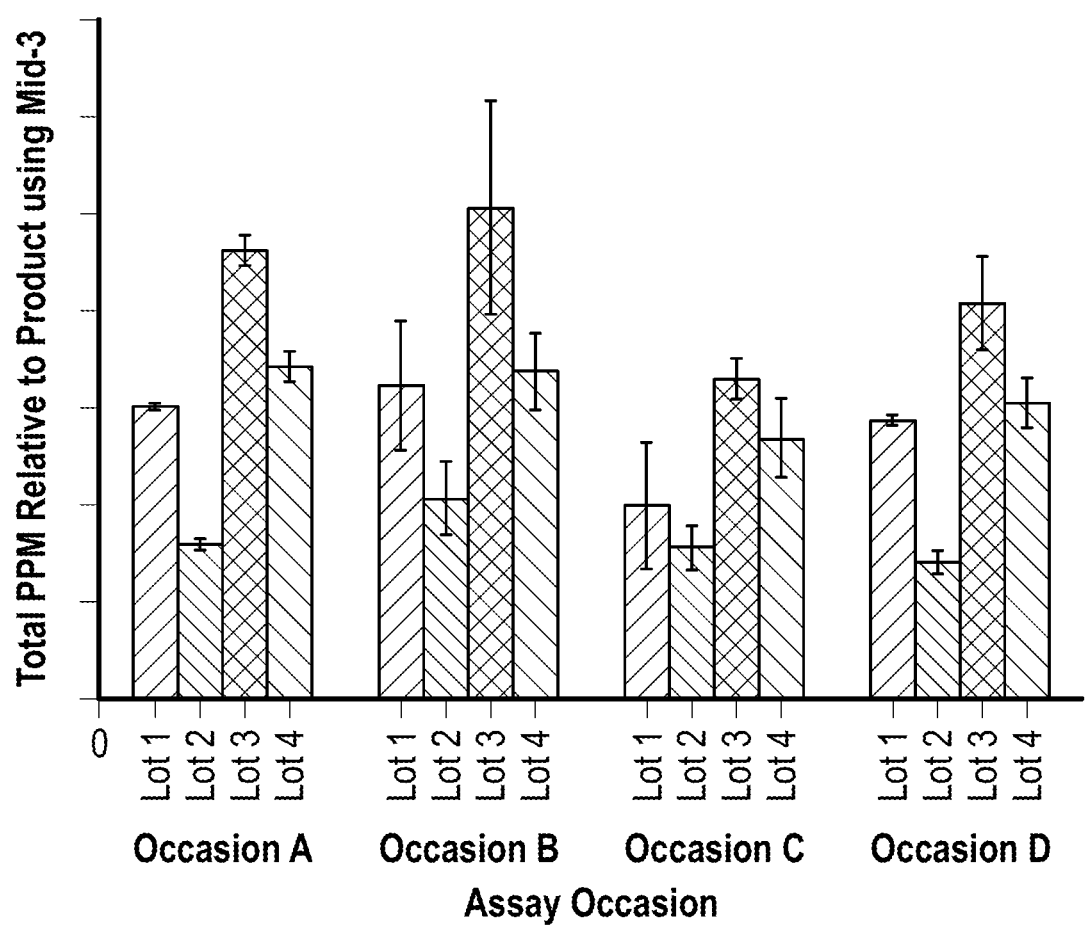

As measured by the Mid-3 method, the total ppm of host cell protein (HCP) was plotted for each protein production lot (FIG. 3B). The quantification measurements of the Mid-3 method have 16% relative standard deviation.

The equation used to calculate polypeptide quantity for the Mid-3 method is as follows:

[(Sum of peak area of top 3 peptide product ions of HCP at the high sample quantity load)/(Sum of peak area of middle 3 peptide product ions of the therapeutic protein product at the high sample quantity load)]*(fmol of the therapeutic protein product at high sample quantity load)* [(Sum of peak area of middle 3 peptide product ions of the therapeutic protein product at the low sample quantity load)/(Sum of peak area of top 3 peptide product ions of the therapeutic protein product at the low sample quantity load)].

Using the Hi-3 method with 200 fmol of ClpB peptides as the internal standard yielded higher error, as compared to the Mid-3 method. Absolute quantitation was much more reproducible using the Mid-3 method. The biggest variability was due to the spiked-in internal standard, although differences in enzymatic digestion may have also occurred. At 10 µg on-column, the middle set of peptide products were more appropriate to use for quantification as they behaved linearly.

Example 3

Application of Mid-3 Quantification Method for Detection and Tracking of Host Cell Proteins During Purification of a Therapeutic Protein This example demonstrates an application of the Mid-3 quantification method disclosed herein for high-throughput detection and tracking of contaminant host cell proteins (HCPs) at multiple stages during a purification process of a therapeutic protein, including samples collected from a cell culture harvest to samples collected following a final desalting protocol. This example further demonstrates use of software for tracking peptides of HCPs by retention time and m/z for label-free quantitation of HCPs in late-stage purification samples, and use of spectral library-based searches to further improve throughput and optimize absolute quantitation.

Methods:

Following cell culture-based production of a therapeutic protein (protein X), samples were collected from the cell culture harvest and at 5 stages of a protein purification process, including final drug substance samples. Using triplicates provided statistical power of downstream measurements, including reproducibility and yield data. After the samples were collected, harvest samples were filtered through a 3k MWCO Amicon Ultra-15 filter (EMD Millipore) according to the manufacturer's instructions to concentrate and remove additives that impede mass spectrometric analysis before being denatured and digested with the rest of the samples. Briefly, a water rinse step of Amicon devices was completed and then 400 µg total protein or therapeutic protein per sample was added with the 50 mM ammonium bicarbonate (Ambic) added on top to a total volume of 15 mL. Subsequently, a wash of 15 mL of 50 mM Ambic was completed, prior to a final centrifugation step. Final concentrations were measured as between 1.4 and 1.7 mg/mL total protein or therapeutic protein. Triplicate aliquots from each sample (from Amicon-filtered harvest through drug substance (DS), as well as a blank digest) were diluted to 1 mg/mL in 50 mM Ambic, and mixed 1:1 with Rapigest (Waters, reconstituted with 50 mM Ambic to a concentration of 0.1%), creating a final solution of 0.5 mg/mL protein in 0.05% Rapigest, 50 mM Ambic. Samples were incubated at 60° C. for 15 minutes to ensure denaturation of the proteins. Reduction of the disulfides was performed with 10 mM 1,4-dithiothreitol (DTT) (Pierce) in 50 mM Ambic at 60° C. for 1 hour. Samples were allowed to cool to room temperature before alkylation with 20 mM 2-Iodoacetamide (IAA) (Pierce) in 50 mM Ambic and incubated at room temperature in the dark for 30 minutes. Lys-C (Promega, 15 µg/vial) was reconstituted in 50 mM Ambic at a concentration of 0.125 µg/µL and added to each sample at an enzyme:substrate ratio of 1:50. The samples were incubated overnight at 37° C. The next morning, trypsin (Promega, 100 µg/vial) solution was prepared at 0.4 µg/µL in 50 mM Ambic and added to the sample at a 1:25 ratio and incubated at 37° C. for 3 hours. Rapigest was removed by acid cleavage with the addition of 2.05% formic acid (EMD Millipore). The samples were incubated for 30 minutes at 37° C. before being centrifuged at 12,000 rpm for 15 minutes to pellet the cleaved Rapigest and any undigested protein. Each autosampler vial was prepared with 20 µg of digested sample, 400 fmol of Hi3 *E. coli* standard (Waters) and diluted to a final volume of 60 µL with 0.1% formic acid for injection on the LC-MS.

The digested samples (30 µL or 10 µg on column) were injected onto a Waters ACQUITY H-Class UPLC system attached to a Waters XEVO G2-XS QTof mass spectrometer for LC-MS analysis using a 1.7 µm CSH C18 Column (2.1 mm×150 mm, Waters). The mass spectrometer was set to collect MSE data over the mass range of 50 to 2000 with 0.3 second scans in sensitivity mode. All samples were run in random order within cleanliness stage (i.e., blanks and drug substance randomized together and run first; mid-process column eluate samples randomized and run next; and cell culture harvest randomized and run last). The UPLC used water and acetonitrile (ACN) with 0.1% formic acid as additives and a gradient of 5 to 40% ACN over 30 minutes, ramping to 85% ACN over 5 minutes, holding for 2 minutes, and returning to initial conditions over 3 minutes, and holding for 5 minutes with a flow rate of 250 µL/min and total gradient time of 45 minutes.

The MS data files were imported into Progenesis Qi for Proteomics software (Nonlinear Dynamics) for peak picking and precursor/product ion alignment before being searched against a sequence database using the MSE search algorithm (Waters). The database combined therapeutic protein product sequences, common contaminant proteins, the Chinese hamster Uniprot database, and a reversed version of each (69,916 total sequences). Identifications were performed with the requirement of 3 fragments per peptide, 7 fragments per protein, and at least 2 peptides per protein with a 4% or less FDR. Further filtering was employed to obtain <1% FDR using a peptide score >5 and peptide mass error <10 ppm. Generally, the peptide identifications were made in the most upstream process samples, e.g., harvest samples, but this was not always the case. Peptides that did not match the trend for the protein were not included for quantitation. The proteins were quantified based on the abundance of the top three peptides per protein (over all three injections) compared to the top three peptides for ClpB (Hi-3) or the linearly-behaving peptides to the product (Mid-3) to determine the relative amount of proteins present in each sample.

Results and Discussion:

One risk of using proteomics discovery software tools for the analysis of relatively low-abundance HCPs in a therapeutic protein production mixture is that abundant ions from the therapeutic protein can be incorrectly identified as HCPs. Recently it has been shown that artifacts on abundant proteins can be identified incorrectly as other proteins at a rate that is much higher than the decoy rate (Kong et al. *Nature methods*. 2017; 14(5):513-520). It is also possible that HCPs may also be identified correctly at the protein level, but some peptides to those HCPs might be incorrect or could be interfered with by other ions, so they should not be used for quantitation.

The method disclosed herein uses the orthogonal physiochemical property of the intensity pattern throughout the purification process to filter out such false positive identifications as well as peptides with interferences. Within Progenesis Qi for Proteomics, each peptide was listed along with the identification score and mass accuracy, as well as a visualization of the peptide trend in the entire experiment. An image showing the detection of each peptide in m/z and retention time was also shown so that other interfering ions can be observed. Peptides having, e.g., observed interference, were not used for quantification.

Figure 4:
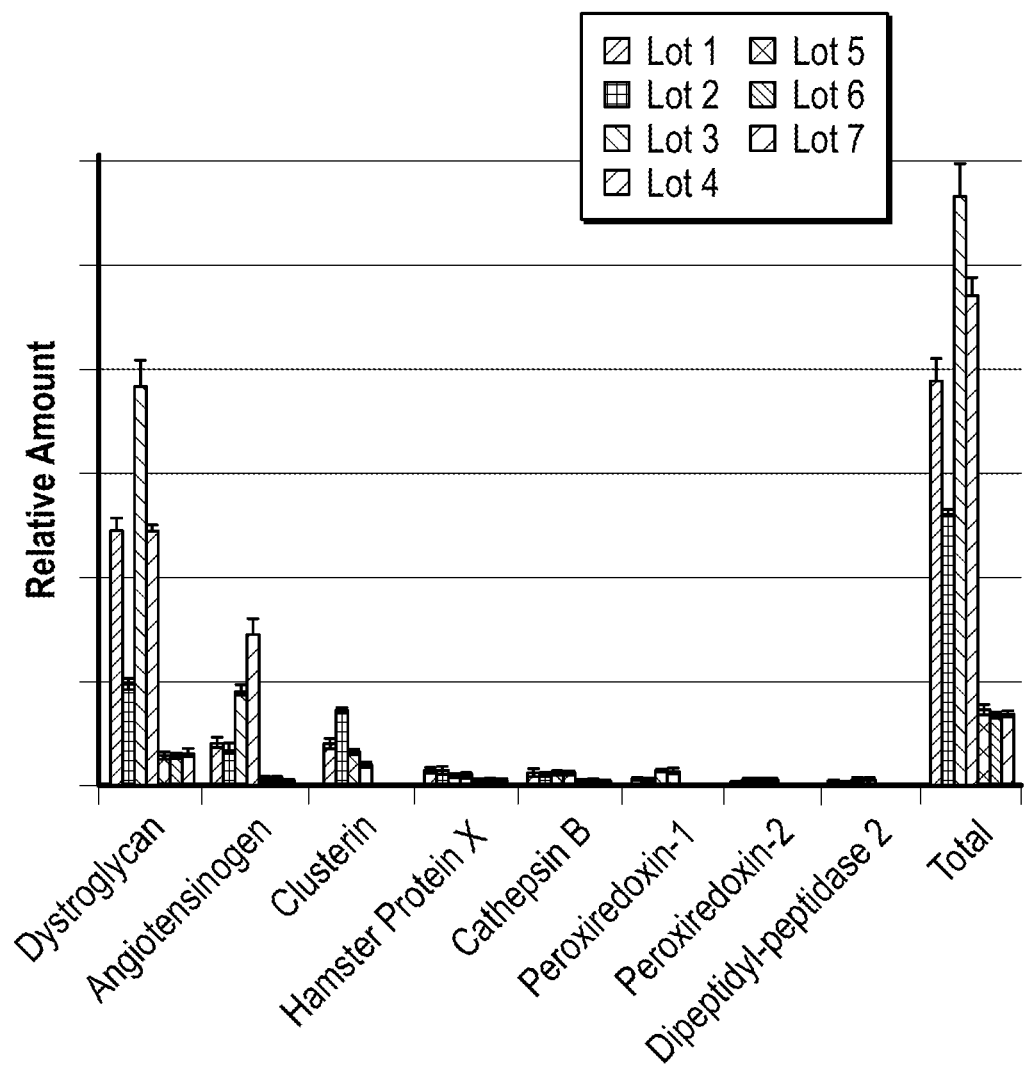
FIG. 4 shows the relative abundance of the top 8 identified host cell proteins across various therapeutic protein production lots.
Figure 5:
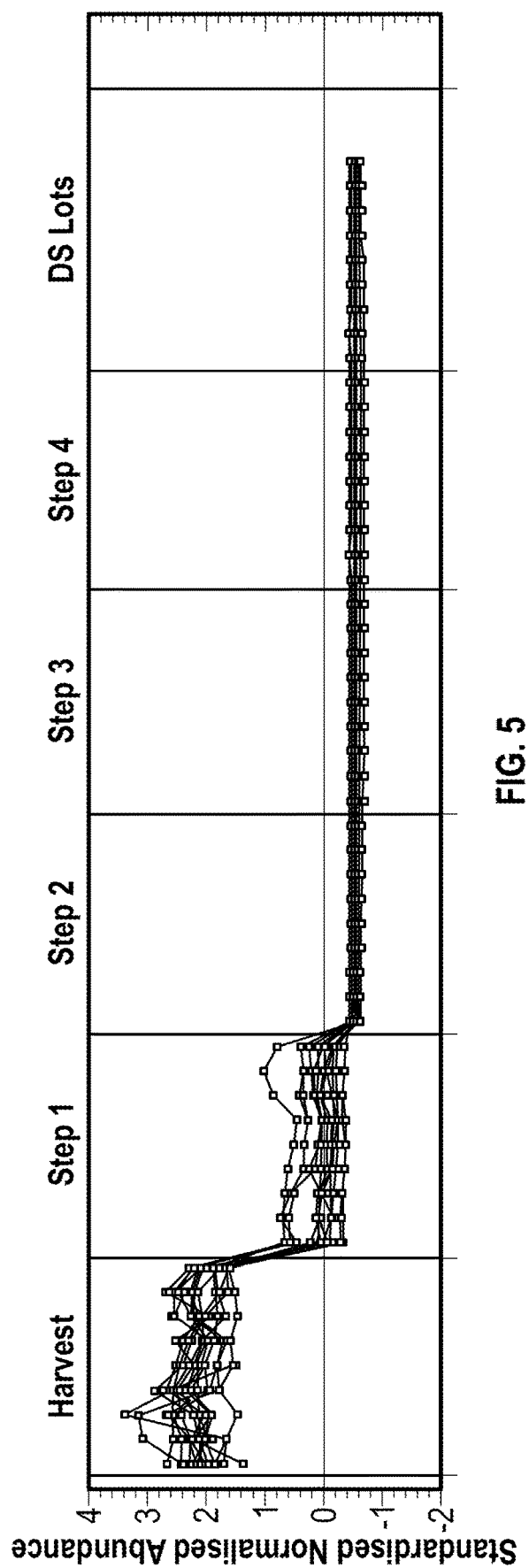
FIG. 5 shows the relative abundance of identified host cell proteins across stages of a purification process for a therapeutic protein.

The LC-MS analysis time for the analysis of samples from the entire purification process was completed in about two days (LC-MS analysis time for a single sample was about 45 minutes). Manually validating the identification of all peptides, including peptides from HCPs, took approximately two weeks. After validation, a final list of identified HCPs from the therapeutic protein production samples was quantified. As shown in FIG. 4, common HCPs were identified between seven production lots. Statistical analyses were performed to understand the purification process, e.g., Principal Components Analysis (PCA), which provided an illustration of the removal of the HCPs during each step of the purification process. Further analysis of the HCPs included hierarchical clustering, which groups proteins that behave similarly during the purification process. The hierarchical clustering allowed for investigation of nodes to discover which proteins are being removed during each step in the purification process. These data were used to understand and optimize the purification processes to ensure that specific HCPs were eliminated from the final therapeutic protein product. HCPs that were not adequately purified from the therapeutic protein were removed by optimizing the purification process based on, e.g., the physiochemical properties of the HCPs, including pI, molecular weight, hydrophobicity, activity, and immunogenicity. The software was also used to automatically monitor the presence of HCPs over the course of a purification process.

The biggest source of variability in the absolute quantitation of HCPs between assay occasions has been either the amount of spiked internal standard or the amount of that peptide-level internal standard to the HCPs, which are digested proteins. The spiked internal standard was usually the Hi-3 ClpB peptides that are meant to be used for absolute quantitation. Great care was taken to solubilize, aliquot, and store the standard, but variability may have occurred due to pipetting differences between, e.g., operators or changes in enzymatic digestion between assay occasions. Instead of using a spiked internal standard, as shown herein, peptides of the therapeutic protein can be used, however, the most abundant peptides from the therapeutic protein are often in an abundance that is beyond the dynamic range of the mass spectrometer, i.e. the most abundant peptides of a therapeutic protein may over saturate the detector of the mass spectrometer. Using the most abundant peptide method (Hi-3 method), the most abundant peptides were observed to have non-linear behavior due to, e.g., detector saturation. In contrast, the peptides in the middle of the ionization distribution, which are called the Mid-3 peptides, were observed to have a linear behavior of signal based on abundance. As shown herein, the Mid-3 peptide method, which incorporates data from the Mid-3 peptides, yielded a lower error and displayed linear behavior up to 18 µg on-column.

What is claimed is:

1. A method for absolute quantification of a first polypeptide in a sample comprising a plurality of polypeptides comprising the first polypeptide and a second polypeptide, wherein the first polypeptide is at least 10-fold lower in abundance than the second polypeptide,
the method comprising:
   (a) analyzing peptide products of the plurality of polypeptides at a plurality of sample loading quantities using a liquid chromatography/mass spectrometry (LC/MS) technique to obtain MS signals of ions of the peptide products of the plurality of polypeptides at each of the plurality of sample loading quantities,
      wherein the plurality of sample loading quantities comprises a first sample loading quantity and a second sample loading quantity, and
      wherein the first sample loading quantity is greater than the second sample loading quantity;
   (b) calculating the average or sum of an MS signal for:
      (i) a top set of n number of qualified ions of peptide products of the first polypeptide with the highest MS signals at the first sample loading quantity (A);
      (ii) a top set of n number of qualified ions of peptide products of the second polypeptide with the highest MS signals at the second sample loading quantity (B);
      (iii) a middle set of m number of qualified ions of peptide products of the second polypeptide at the first sample loading quantity (C),
         wherein the middle set of qualified ions of the peptide products of the second polypeptide has a lower quantification error than the top set of qualified ions of the peptide products of the second polypeptide for the first sample loading quantity and the second sample loading quantity; and
      (iv) the middle set of qualified ions of peptide products of the second polypeptide at the second sample loading quantity (D),
         wherein A, B, C, and D are all calculated using the average or all calculated using the sum of the MS signal; and
   (c) determining an absolute quantity of the first polypeptide in the first sample loading quantity based on the following formula:

$$[(A)/(C)]*(\text{mole of the second polypeptide at the first loading quantity})*[(D)/(B)],$$

or mathematical equivalents thereof.

2. A method for absolute quantification of a first polypeptide in a sample comprising a plurality of polypeptides comprising the first polypeptide and a second polypeptide, wherein the first polypeptide is at least 10-fold lower in abundance than the second polypeptide,
the method comprising:
   (a) obtaining MS signals of ions of peptide products of the plurality of polypeptides,
      wherein said MS signals of ions of the peptide products are obtained by analyzing the peptide products of the plurality of polypeptides using a liquid chromatography/mass spectrometry (LC/MS) technique,
      wherein MS signals of the peptide products are obtained for each of a plurality of sample loading quantities comprising a first sample loading quantity and a second sample loading quantity, and
      wherein the first sample loading quantity is greater than the second sample loading quantity;
   (b) calculating the average or sum of an MS signal for:
      (i) a top set of n number of qualified ions of peptide products of the first polypeptide with the highest MS signals at the first sample loading quantity (A);
      (ii) a top set of n number of qualified ions of peptide products of the second polypeptide with the highest MS signals at the second sample loading quantity (B);
      (iii) a middle set of m number of qualified ions of peptide products of the second polypeptide at the first sample loading quantity (C),
         wherein the middle set of qualified ions of the peptide products of the second polypeptide has a lower quantification error than the top set of qualified ions of the peptide products of the second polypeptide for the first sample loading quantity and the second sample loading quantity; and
      (iv) the middle set of qualified ions of peptide products of the second polypeptide at the second sample loading quantity (D),
         wherein A, B, C, and D are all calculated using the average or all calculated using the sum of the MS signal; and
   (c) determining an absolute quantity of the first polypeptide in the first sample loading quantity based on the following formula:

$$[(A)/(C)]*(\text{mole of the second polypeptide at the first loading quantity})*[(D)/(B)],$$

or mathematical equivalents thereof.

3. The method of claim 2, wherein the middle set of qualified ions of peptide products of the second polypeptide is selected based on quantification error of the qualified ions of peptide products of the second polypeptide from (1) the plurality of sample loading quantities, or (2) the first sample loading quantity and/or the second sample loading quantity.

4. The method of claim 3, further comprising selecting the middle set of qualified ions of peptide products of the second polypeptide.

5. The method of claim 2, wherein each of the top set of qualified ions of peptide products is different than each of the middle set of qualified ions.

6. The method of claim 2, wherein the MS signal is ionization intensity, peak height, peak area, or peak volume.

7. The method of claim 2, wherein the LC/MS technique further comprises one or more the following:

(a) identifying the peptide products by amino acid sequence;
(b) identifying the first polypeptide by a protein identifier; and
(c) identifying one or more of the plurality of polypeptides by a protein identifier.

8. The method of claim 2, further comprising determining the absolute quantity of the second polypeptide.

9. The method of claim 2, wherein the first polypeptide is a host cell protein and/or a biomarker.

10. The method of claim 2, wherein the first polypeptide is at least 100-fold lower in abundance than the second polypeptide.

11. The method of claim 2, wherein the second polypeptide is a recombinant polypeptide produced by a host cell and/or a therapeutic polypeptide.

12. The method of claim 2, wherein the sample is a cell culture sample, a blood sample, or a serum sample.

13. The method of claim 12, wherein the sample is a blood sample or serum sample, and wherein the second polypeptide is serum albumin.

14. The method of claim 2, wherein the sample is a pharmaceutical product or an intermediate thereof.

15. The method of claim 2, further comprising selecting the second sample loading quantity based on MS signals of the second set of peptide products and/or selecting the first sample loading quantity based on MS signals of the first set of peptide products.

16. The method of claim 2, wherein n and/or m is 3.

17. The method of claim 2, wherein the middle set of qualified ions of peptide products of the second polypeptide are selected based on the sequences of each of the peptide products.

18. A method for detecting a contaminate polypeptide in the production of a therapeutic polypeptide, the method comprising:
(a) obtaining a sample comprising the therapeutic polypeptide;
(b) determining if the contaminate polypeptide is present in the sample;
wherein the presence of the contaminate polypeptide is based on the absolute quantification of the contaminate polypeptide in the sample using the method of claim 2.

* * * * *